(12) United States Patent
Fujishima et al.

(10) Patent No.: US 6,608,092 B1
(45) Date of Patent: *Aug. 19, 2003

(54) CRYSTALS OF BENZIMIDAZOLE COMPOUNDS

(75) Inventors: Akira Fujishima, Sanda (JP); Isao Aoki, Kawanishi (JP); Keiji Kamiyama, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/019,254
(22) PCT Filed: Jun. 29, 2000
(86) PCT No.: PCT/JP00/04279
§ 371 (c)(1), (2), (4) Date: Dec. 28, 2001
(87) PCT Pub. No.: WO01/02389
PCT Pub. Date: Jan. 11, 2001

(30) Foreign Application Priority Data

Jun. 30, 1999 (JP) .......................................... 11-186403

(51) Int. Cl.⁷ .................. C07D 401/12; A61K 31/4439
(52) U.S. Cl. ..................................... 514/338; 546/273.7
(58) Field of Search ..................... 514/338; 546/273.7

(56) References Cited

U.S. PATENT DOCUMENTS 4,628,098 A  12/1986  Nohara et al. ............... 546/271
6,462,058 B1 * 10/2002 Fujishima et al. .......... 514/338

FOREIGN PATENT DOCUMENTS

| EP | 0 174 726 | | 3/1986 |
| EP | 302720 | * | 2/1989 |
| WO | 96/02535 | | 2/1996 |
| WO | 96/17077 | | 6/1996 |
| WO | 97/02261 | | 1/1997 |
| WO | 98/21201 | | 5/1998 |
| WO | 9208716 | * | 5/1999 |
| WO | 99/38512 | | 8/1999 |

OTHER PUBLICATIONS

CA 127:336721, Curin et al., 1997.*
CA 127:362535, Vrecer et al. 1997.*
H. Nagaya et al., "Effects of the Enantiomers of Lansoprazole (AG–1749) on ($H^+$+$K^+$)–ATPase Activity in Canine Gastric Microsomes and Acid Formation in Isolated Canine Parietal Cells", Biochemical Pharmacology, vol. 42, No. 10. pp. 1875–1878, 1991.
H. Katsuki et al., "Determination of R(+)– and S(–)–Lansoprazole Using Chiral Stationary–Phase Liquid Chromatography and Their Enantioselective Pharmacokinetics in Humans", Pharmaceutical Research, vol. 13, No. 4, pp. 611–615, 1996.

* cited by examiner

*Primary Examiner*—Jane Fan
(74) *Attorney, Agent, or Firm*—Wenderoth, Lind & Ponack, L.L.P.

(57) ABSTRACT

Crystals of (S)-2[[[3-methyl-4-(2,2,2-trifluoroethoxy)-2-pyridinyl]methyl]sulfinyl]-1H-benzimidazole or salts thereof, useful as excellent antiulcer drugs.

4 Claims, No Drawings

CRYSTALS OF BENZIMIDAZOLE COMPOUNDS

This application is a 371 of PCT/JP00/04279 filed Jun. 29, 2000.

TECHNICAL FIELD

The present invention relates to crystals of a benzimidazole compound that possesses an antiulcer action.

BACKGROUND ART

2-[[[3-Methyl-4-(2,2,2-trifluoroethoxy)-2-pyridinyl]methyl]sulfinyl]-1H-benzimidazole or a salt thereof, which possess an antiulcer activity, has been described in JP 61-50978 A and the like.

DISCLOSURE OF THE INVENTION

2-[[[3-Methyl-4-(2,2,2-trifluoroethoxy)-2-pyridinyl]methyl]sulfinyl]-1H-benzimidazole possesses a chiral sulfur within the molecule, and two kinds of optical isomers thereof exist. As a result of intensive investigations, the present inventors have succeeded in the optical resolution and crystallization of the (S) isomer of 2-[[[3-methyl-4-(2,2,2-trifluoroethoxy)-2-pyridinyl]methyl]sulfinyl]-1H-benzimidazole and have found for the first time that the crystals are satisfactory enough for drugs, thereby having completed the present invention on the basis of these findings.

In other words, the present invention relates to
(1) crystals of (S)-2-[[[3-methyl-4-(2,2,2-trifluoroethoxy)-pyridinyl]methyl]sulfinyl]-1H-benzimidazole or a salt thereof,
(2) crystals of (S)-2-[[[3-methyl-4-(2,2,2-trifluoroethoxy)-pyridinyl]methyl]sulfinyl]-1H-benzimidazole,
(3) the crystals as described in the above (2) which possess a pattern of the powder X-ray diffraction whose characteristic peaks appear at the lattice spacing (d) of the powder X-ray diffraction of 11.68, 6.78, 5.85, 5.73, 4.43, 4.09, 3.94, 3.90, 3.69, 3.41, 3.11 angstrom (Å),
(4) a pharmaceutical composition comprising the crystals as described in the above (1) and the like.

As for the "salt" of "(S)-2-[[[3-methyl-4-(2,2,2-trifluoroethoxy)-2-pyridinyl]methyl]sulfinyl]-1H-benzimidazole or a salt thereof", a physiologically acceptable salt is preferred, which is exemplified by a metal salt, a salt with an organic base, a salt with a basic amino acid or the like.

Examples of a metal salt include an alkaline metal salt such as sodium salt, potassium salt, etc., an alkaline earth metal salt such as calcium salt, magnesium salt, barium salt, etc., and the like. A salt with an organic base is exemplified by a salt with trimethylamine, triethylamine, pyridine, picoline, ethanolamine, diethanolamine, triethanolamine, dicyclohexylamine, N,N-dibenzylethylenediamine or the like. A salt with a basic amino acid is exemplified by a salt with arginine, lysine or the like.

Crystals of (S)-2-[[[3-methyl-4-(2,2,2-trifluoroethoxy)-2-pyridinyl]methyl]sulfinyl]-1H-benzimidazole or a salt thereof may be a hydrate or a non-hydrate.

Said "hydrate" is exemplified by a 0.5 to 5.0 hydrate. Among them, 0.5 hydrate, 1.0 hydrate, 1.5 hydrate, 2.0 hydrate, or 2.5 hydrate is preferable. Particularly preferred is 1.5 hydrate.

Crystals of (S)-2-[[[3-methyl-4-(2,2,2-trifluoroethoxy)-2-pyridinyl]methyl]sulfinyl]-1H-benzimidazole or a salt thereof can be obtained by subjecting 2-[[[3-methyl-4-(2,2,2-trifluoroethoxy)-2-pyridinyl]methyl]sulfinyl]-1H-benzimidazole or a salt thereof to optical resolution or by subjecting 2-[[[3-methyl-4-(2,2,2-trifluoroethoxy)-2-pyridinyl]methyl]thio]-1H-benzimidazole or a salt thereof to asymmetric oxidation to obtain the (S)-isomer, followed by crystallization.

Examples of a method used for the optical resolution include a per se known method such as a fractional recrystallization method, a chiral column method, a diastereomer method and the like. As asymmetric oxidation, a per se known method is used.

The "fractional recrystallization method" is exemplified by a method, in which the racemate is treated with an optically active compound [e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine, etc.) to form the salts, followed by separation by a fractional recrystallization or the like, and, optionally, by subjecting the resultant to a neutralization step to obtain the optical isomer in the free form.

The "chiral column method" is exemplified by a method, in which the racemate or a salt thereof is applied to a column for separation of optical isomers (a chiral column). In the case of liquid chromatography, for instance, there is exemplified a method, in which the racemate is added to a chiral column such as ENANTIO-OVM (manufactured by Toso Corporation), CHIRAL series manufactured by Daicel Company or the like, which is eluted with water, a buffer solution (e.g., a phosphate buffer solution), an organic solvent (e.g., hexane, ethanol, methanol, isopropanol, acetonitrile, trifluoroacetic acid, diethylamine, triethylamine, etc.) or a mixed solvent thereof to separate the optical isomers. In the case of gas chromatography, for instance, a separation method using a chiral column such as CP-Chirasil-DeX CB (manufactured by G-L Sciences Inc.) or the like is exemplified.

The "diastereomer method" is exemplified by a method, in which the racemate is allowed to react with an optically active reagent (preferably, to react with the optically active reagent at position 1 of the benzimidazole group) to obtain a mixture of the diastereomers, followed by treatment with a conventional separation means (e.g., fractional recrystallization, chromatography method, etc.) to obtain one of the diastereomers, which is then subjected to a chemical reaction (e.g., acid hydrolysis reaction, basic hydrolysis reaction, hydrogenolysis reaction, etc.) to cleave the moiety of the optically active reagent, thereby obtaining the objective optical isomer. Examples of said "optically active reagent" include optically active organic acids such as MTPA [α-methoxy-α-(trifluoromethyl)phenylacetic acid], (−)-menthoxyacetic acid and the like; optically active alkoxymethyl halides such as (1R-endo)-2-(chloromethoxy)-1,3,3-trimethylbicyclo[2.2.1]heptane, and the like.

2-[[[3-Methyl-4-(2,2,2-trifluoroethoxy)-2-pyridinyl]methyl]sulfinyl]-1H-benzimidazole or a salt thereof is produced according to the method described in JP 61-50978 A, U.S. Pat. No. 4,628,098 or the like, or a modified method thereof.

Examples of the method for crystallization include a per se known method such as crystallization from a solution, crystallization from a vapor, and crystallization from a melt.

Examples of the method for said "crystallization from a solution" include a concentration method, a slow cooling method, a reaction method (diffusion method or electrolysis method), a hydrothermal formation method, a fluxing agent method and the like. Examples of the solvent to be used include aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitrites (e.g., acetonitrile, etc.), ketones (e.g., acetone, etc.), sulfoxides (e.g., dimethyl sulfoxide, etc.), acid amides (e.g., N,N-dimethylformamide, etc.), esters (e.g., ethyl acetate, etc.), alcohols (e.g., methanol, ethanol, isopropyl alcohol, etc.), water and the like. These solvents are used alone or in combination of two or more thereof in an adequate ratio (for example, 1:1 to 1:100).

Examples of the method for said "crystallization from a vapor" include an evaporation method (a sealed tube method or an air stream method), a vapor phase reaction method, a chemical transportation method or the like.

Examples of the method for said "crystallization from a melt" include a normal freezing method (pulling-up method, temperature gradient method or Bridgman method), a zone melting method (zone leveling method or float zone method), a special growth method (VLS method or liquid-phase epitaxy method) and the like.

As for an method for analyzing the thus-obtained crystals, generally, crystal analysis by a X-ray diffraction method is employed. Furthermore, a method for determining the orientation of crystals is exemplified by a mechanical method, an optical method or the like.

The thus-obtained crystals of (S)-2-[[[3-methyl-4-(2,2,3-trifluoroethoxy)-2-pyridinyl]methyl]sulfinyl]-1H-benzimidazole or a salt thereof (hereinafter, sometimes, abbreviated as "the crystals of the present invention") possesses an excellent antiulcer activity, an anti-gastric acid secreting activity, a mucous membrane protecting activity, an anti-*Helicobacter pylori* activity and the like, and is useful as drugs owing to the low toxicity. Moreover, crystallization of the S-form not only increases the stability but also facilitates the handling of the compound, thereby making it possible to manufacture solid pharmaceutical compositions in a reproducible manner. Also, a shorter duration of the pharmacological activity is obtained in the case of administration of the crystals of the present invention, resulting in allowing a long-term administration.

The crystals of the present invention are useful for therapeutics and prophylaxis of a peptic ulcer (e.g., gastric ulcer, duodenal ulcer, stomal ulcer, Zollinger-Ellison's syndrome, etc.), gastritis, reflux esophagitis, NUD (non-ulcer dyspepsia), stomach cancer, gastric MALT lymphoma and the like, eradication of *Helicobacter pylori*, suppression of bleeding of upper gastrointestinal tract caused by peptic ulcer, acute stress ulcer and hemorrhagic gastritis, suppression of bleeding of upper gastrointestinal tract caused by invasive stress (stress caused by major surgery requiring postoperative intensive care, cerebrovascular disorder requiring intensive treatment, head injury, multiple organ failure and extensive burn), therapeutics and prophylaxis of ulcer caused by a nonsteroidal antiinflammatory agent; therapeutics and prophylaxis of hyperacidity and ulcer caused by postoperative stress; pre-anesthetic medication, and the like, in mammals (e.g., human, monkey, sheep, cow, horse, dog, cat, rabbit, rat, mouse, etc.).

The crystals of the present invention are low in the toxicity and can be safely administered orally or parenterally (for example, local, rectal and intravenous administrations, or the like) as they are or as any of pharmaceutical compositions, which are prepared by mixing with pharmacologically acceptable carriers according to a per se known method, such as, for example, tablets (including sugar-coated tablets and film-coated tablets), powders, granular preparations, capsules (including soft capsules), oral disintegrating tablets, solutions, injectable preparations, suppositories, sustained release preparations, patches and the like.

The content of the crystals of the present invention in the pharmaceutical compositions of the present invention is about 0.01 to 100% by weight based on the total weight of the composition. Although the dose of any of said pharmaceutical compositions varies depending on particular patient, route of administration, disease and the like, in the case of oral administration to an adult (60 kg) as an antiulcer agent, for instance, the dose is about 0.5 to 1500 mg/day as the active ingredient, preferably about 5 to 150 mg/day. The daily dosage of the crystals of the present invention may be administered at once or divided into 2 to 3 times per day.

As for the pharmacologically acceptable carriers that may be used for the manufacture of the pharmaceutical compositions of the present invention, there are used a variety of conventional pharmaceutically acceptable organic or inorganic carrier substances, for example, excipients, lubricants, binding agents, disintegrators, water-soluble high molecular substances and basic inorganic salts for solid preparations; solvents, solubilizing agents, suspending agents, isotonicity agents, buffering agents and analgesics for liquid preparations, and the like. Also, as needed, additives such as conventional preservatives, antioxidants, coloring agents, sweeteners, acidifiers, foaming agents, flavors and the like can be used.

Examples of said "excipients" include lactose, white soft sugar, D-mannitol, starch, corn starch, crystalline cellulose, light anhydrous silicic acid, titanium oxide and the like.

Examples of said "lubricants" include magnesium stearate, a sucrose fatty acid ester, polyethylene glycol, talc, stearic acid and the like.

Examples of said "binding agents" include hydroxypropyl cellulose, hydroxypropylmethyl cellulose, crystalline cellulose, α-starch, polyvinyl pyrrolidone, gum arabic, gelatin, Pullulan, low-substituted hydroxypropyl cellulose and the like.

Examples of said "disintegrators" include (1) crospovidon, (2) a disintegrator that is designated as a super disintegrator such as croscarmellose sodium (FMC-Asahi Kasei), carmellose calcium (Gotoku Yakuhin) or the like, (3) carboxymethyl starch sodium (e.g., manufactured by Matsutani Kagaku Kabushiki Kaisha), (4) a low-substituted hydroxypropyl cellulose (e.g., manufactured by Shin-Etsu Kagaku Kabushiki Kaisha), (5) corn starch, and the like. Said "crospovidon" may be any of crosslinked polymers that have a chemical name of 1-ethenyl-2-pyrrolidinone homopolymer, including polyvinyl polypyrrolidone (PVPP) and so-called 1-vinyl-2-pyrrolidinone homopolymer, where specific examples include Kollidon CL (manufactured by BASF AG), Polyplasdon XL (manufactured by ISP Company), Polyplasdon XL-10 (manufactured by ISP Company), Polyplasdon INF-10 (manufactured by ISP Company) and the like.

Examples of said "water-soluble high molecular substances" include an ethanol-soluble, water-soluble high molecular substance [for example, a cellulose derivative such as hydroxypropyl cellulose (hereinafter, may be described as HPC), polyvinyl pyrrolidone and the like], an ethanol-insoluble, water-soluble high molecular substance [for example, a cellulose derivative such as hydroxypropylmethyl cellulose (hereinafter, may be described as HPMC), methyl cellulose or carboxymethyl cellulose sodium, sodium polyacrylate, polyvinyl alcohol, sodium alginate, guar gum and the like] and the like.

Examples of said "basic inorganic salts" include a basic inorganic salt of sodium, potassium, magnesium and/or calcium. Preferably, it is a basic inorganic salt of magnesium and/or calcium. More preferably, it is a basic inorganic salt of magnesium. Examples of said basic inorganic salt of sodium include sodium carbonate, sodium hydrogen carbonate, disodium hydrogen phosphate and the like. Examples of said basic inorganic salt of potassium include potassium carbonate, potassium hydrogen carbonate and the like. Examples of said basic inorganic salt of magnesium include magnesium carbonate heavy, magnesium carbonate, magnesium oxide, magnesium hydroxide, magnesium metasilicate aluminate, magnesium silicate, magnesium aluminate, synthetic hydrotalcite [$Mg_6Al_2(OH)_{16} \cdot CO_3 \cdot 4 H_2O$] and alumina magnesium hydroxide, preferably magnesium carbonate heavy, magnesium carbonate, magnesium oxide, magnesium hydroxide and the like. Examples of said basic inorganic salt of calcium include precipitated calcium carbonate, calcium hydroxide and the like.

Examples of said "solvents" include water for injection, alcohol, propylene glycol, macrogol, sesame oil, corn oil, olive oil and the like.

Examples of said "solubilizing agents" include polyethylene glycol, propylene glycol, D-mannitol, benzyl benzoate, ethanol, trisamiomethane, cholesterol, triethanolamine, sodium carbonate, sodium citrate and the like.

Examples of said "suspending agents" include, a surface active agent such as stearyltriethanolamine, sodium lauryl sulfate, laurylaminopropionic acid, lecithin, benzalkonium chloride, benzethonium chloride, glycerin monostearate or the like; a hydrophilic, high molecular substance such as, for example, polyvinyl alcohol, polyvinyl pyrrolidone, sodium carboxymethyl cellulose, methyl cellulose, hydroxymethyl cellulose, hydroxyethyl cellulose, hydroxypropyl cellulose or the like, and the like.

Examples of said "isotonicity agents" include glucose, D-sorbitol, sodium chloride, glycerin, D-mannitol and the like.

Examples of said "buffering agents" include a buffer solution of a phosphate, an acetate, a carbonate, a citrate or the like, and the like.

Examples of said "analgesics" include benzyl alcohol and the like.

Examples of said "preservatives" include a paraoxybenzoic acid ester, chlorobutanol, benzyl alcohol, phenethyl alcohol, dehydroacetic acid, sorbic acid and the like.

Examples of said "antioxidants" include a sulfite salt, ascorbic acid, α-tocopherol and the like.

Examples of said "coloring agents" include a food dye such as food yellow No. 5, food red No. 2, food blue No. 2 or the like; edible lake dye, iron oxide red and the like.

Examples of said "sweeteners" include saccharin sodium, dipotassium glycyrrhizinate, aspartame, stevia, somatin and the like.

Examples of said "acidifiers" include citric acid (anhydrous citric acid), tartaric acid, malic acid and the like.

Examples of said "foaming agents" include sodium bicarbonate and the like.

Examples of said "flavors", which may be either synthetic or naturally occurring, include lemon, lime, orange, menthol, strawberry and the like.

The oral preparations can be manufactured according to a per se known method by adding to the crystals of the present invention, for examples, a bulking agent, a disintegrator, a binding agent, a lubricant and the like, and by subjecting the resulting mixture to compression molding, as needed, followed by coating according to a per se known method for the purpose of masking of the taste, enteric coating or durability. In the case of the manufacture of an enteric coated preparation, an intermediary phase may be provided between the enteric coated phase and the drug-containing phase, according to a per se known method, for the purpose of separating both phases.

In the case where the crystals of the present invention are used for the manufacture of an oral rapidly disintegrating tablet, there is exemplified a method comprising coating a core containing crystalline cellulose and lactose with the crystals of the present invention and a basic inorganic salt, followed by further coating with a coating layer containing a water-soluble high molecular substance to obtain a composition, coating the thus-obtained composition with an enteric coating layer containing polyethylene glycol, coating with an enteric coating layer containing triethyl citrate, coating with an enteric coating layer containing polyethylene glycol, further coating with mannitol to obtain fine granules, mixing the thus-obtained fine granules with an excipient and molding, or the like. Examples of the above-described "enteric coating layer" include one or more of an aqueous-type enteric high molecular base such as cellulose acetate phthalate (CAP), hydroxypropylmethyl cellulose phthalate, hydroxymethyl cellulose acetate succinate, a methacrylate copolymer [e.g., Eudragit L30D-55 (trade name; manufactured by Rohm Company), Kollicoat MAE30DP (trade name; manufactured by BASF AG), Poliquid PA30 (trade name; manufactured by Sanyo Kasei Company), etc.], carboxymethylethyl cellulose, shellac or the like; a sustained-release base such as a methacrylate copolymer [e.g., Eudragit NE30D (trade name), Eudragit RL30D (trade name), Eudragit RS30D (trade name), etc.] or the like; a water-soluble high molecular substance; plasticizers such as triethyl citrate, polyethylene glycol, acetylated monoglyceride, triacetin, castor oil, etc., and the like. Examples of the above-described "additives" include a water-soluble sugar alcohol (e.g., sorbitol, mannitol, maltitol, reducing saccharized starch, xylitol, reducing palatinose, erythritol, etc.), crystalline cellulose (e.g., Ceolus KG 801, Avicel PH 101, Avicel PH 102, Avicel PH 301, Avicel PH 302, Avicel RC-591 (crystalline cellulose/carmellose sodium), etc.), a low substitution degree hydroxypropyl cellulose (e.g., LH-22, LH-32, LH-23, LH-33 (Shin-Etsu Kagaku Kabushiki Kaisha), a mixture thereof, etc.) or the like, where there are further used a binding agent, an acidifier, a foaming agent, a sweetener, a flavor, a lubricant, a coloring agent, a stabilizer, an excipient, a disintegrator and the like.

The crystals of the present invention may be used together with 1 to 3 kinds of other active components.

Examples of said "other active components" include an anti-*Helicobacter pylori* substance, an imidazole compound, a bismuth salt, a quinolone compound and the like. Among these, an anti-*Helicobacter pylori* substance, an imidazole compound and the like are preferable. Examples of said "anti-*Helicobacter pylori* substance" include a penicillin antibiotic (e.g., amoxicillin, benzyl penicillin, piperacillin, mecillinam, etc.), a cephem antibiotic (e.g., cefixime, cefaclor, etc.), a macrolide antibiotic (e.g., erythromycin, clarithromycin, etc.), a tetracycline antibiotic (e.g., tetracycline, minocycline, streptomycin, etc.), an aminoglycoside antibiotic (e.g., gentamycin, amikacin, etc.), imipenem and the like. A penicillin antibiotic, a macrolide antibiotic and the like are especially preferable. Examples of said "imidazole compound" include metronidazole, miconazole and the like. Examples of said "bismuth salt" include bismuth acetate, bismuth citrate and the like. Examples of said "quinolone compound" include ofloxacin, ciproxacin and the like.

Said "other active components" and the crystals of the present invention may be mixed and formulated into a single pharmaceutical composition (e.g., a tablet, a powder, a granule preparation, a capsule (including a soft capsule), a liquid and solution, an injection, a suppository, a sustained release preparation, etc.) according to a per se known method, or may be formulated separately and administered to the same subject at the same time or at a certain interval.

The following Reference Examples and Examples further illustrate the present invention in more detail, but they are not intended to limit the present invention.

In the following Reference Examples and Examples, room temperature means a temperature of about 15 to 30° C.

The melting points were measured by the use of a Micro Melting Point Apparatus (manufactured by Yanagimoto Seisakusho), and uncorrected values are shown.

The $^1$H-NMR spectra were measured by the use of a Varian Gemini-2000 using $CDCl_3$ as a solvent, and the chemical shifts δ (ppm) from tetramethylsilane used as the internal standard are shown.

The IR spectra were measured with a SHIMAZU FTIR-8200.

The UV spectra were measured with a HITACHI U-3200 Spectrophotometer.

The optical rotations [$α_D$] were measured at 20° C. by the use of a DIP-370 Digital polarimeter (manufactured by Nihon Bunko (JASCO)).

The measurement of optical purity was conducted by HPLC using a chiral column (column: CHIRALCEL OD 4.6 mm φ×250 mm, temperature: about 20° C., mobile phase: hexane/2-propanol=80/20 or hexane/2-propanol=85/15, flow rate: 1.0 mL/minute, detection wavelength: 285 nm).

The crystal data of X-ray diffraction analysis for determining the absolute structure of the sulfoxide were measured by the use of a 4-circle diffractometer (RIGAKU AFC5R) using the Cu-Kα radiation. An initial phase was determined by the direct method, and the structure was refined with a SHELXL-93. The powder X-ray diffraction was measured by the use of an X-ray Powder Diffractometer Rigaku RINT 2500 (ultra X18) No. PX-3.

The other symbols in the present specification indicate the following meanings.

S: singlet d: doublet t: triplet q: qualtet m: multiplet bs: broad singlet

J: coupling constant

REFERENCE EXAMPLE 1

Preparative Separation of (S)-2-[[[3-Methyl-4-(2,2,2-trifluoroethoxy)-2-pyridinyl]methyl]sulfinyl]-1H-benzimidazole (S(−)-Lansoprazole)

2-[[[3-Methyl-4-(2,2,2-trifluoroethoxy)-2-pyridinyl] methyl]sulfinyl]-1H-benzimidazole (lansoprazole) (racemate) (3.98 g) dissolved in the mobile phase described below (330 mL) and acetonitrile (37 mL) was fractionated by HPLC (column: CHIRALCEL OD 20 mm φ×250 mm, temperature: 30° C., mobile phase: hexane/2-propanol/ethanol=255/35/10, flow rate: 16 mL/minute, detection wavelength: 285 nm, one shot: 20 to 25 mg). The fractions of the optical isomer having a longer retention time were collected and were concentrated, all lots were combined and were dissolved in ethanol, the resulting solution was filtered through a 0.45 μm filter and the filtrate that was mixed with hexane was evaporated to dryness again to obtain S(−)-lansoprazole (1.58 g, an optical purity of 92.6% ee) as an amorphous material.

The thus-obtained amorphous material was fractionated again in the same way as described above to obtain S(−)-lansoprazole (0.94 g, an optical purity of 99.0% ee) as an amorphous substance.

[$α_D$]=−175.4° (c=1.003%, $CHCl_3$)

REFERENCE EXAMPLE 2

Preparative Separation of (S)-2-[[[3-Methyl-4-(2,2,2-trifluoroethoxy)-2-pyridinyl]methyl]sulfinyl]-1H-benzimidazole (S(−)-Lansoprazole)

Lansoprazole (racemate) (34.2 g) dissolved in 2-propanol (1710 mL) and hexane (1140 mL) containing triethylamine (0.2%) was fractionated by HPLC (column: CHIRALCEL OD 50 mm φ×500 mm, temperature: room temperature, mobile phase: hexane/2-propanol =85/15, flow rate: 60 mL/minute, detection wavelength: 285 nm, one shot: about 300 mg). The fractions of the optical isomer having a longer retention time were collected and were concentrated, all lots were.combined and were dissolved in ethanol (250 mL) and the resulting solution, into which triethylamine (3 mL) was added, was then filtered through a 0.45 μm filter. The filtrate was concentrated, was mixed with hexane and was evaporated again to dryness to obtain S(−)-lansoprazole (9.15 g, an optical purity of 93.3% ee) as an amorphous substance.

REFERENCE EXAMPLE 3

Preparative Separation of (S)-2-[[[3-Methyl-4-(2,2,2-trifluoroethoxy)-2-pyridinyl]methyl]sulfinyl]-1H-benzimidazole (S(−)-Lansoprazole)

Lansoprazole (racemate) (4.1 g) dissolved in the mobile phase described below (100 mL) and ethanol (100 mL) was fractionated by HPLC (column: CHIRALCEL OD 50 mm φ×500 mm, temperature: 30° C., mobile phase: hexane/2-propanol=85/15, flow rate: 60 mL/minute, detection wavelength: 285 nm, one shot: 260 to 300 mg). The fractions of the optical isomer having a longer retention time were collected and were concentrated, all lots were combined and were dissolved in ethanol, the resulting solution was filtered through a 0.45 μm filter and the filtrate that was mixed with hexane was evaporated to dryness again to obtain S(−)-lansoprazole (1.6 g) as an amorphous material.

The thus-obtained amorphous material was fractionated again in the same way as described above to obtain S(−)-lansoprazole (1.43 g, an optical purity of 97.4% ee) as an amorphous substance.

EXAMPLE 1

Crystals of (S)-2-[[[3-Methyl-4-(2,2,2-trifluoroethoxy)-2-pyridinyl]methyl]sulfinyl]-1H-benzimidazole (S(−)-Lansoprazole)

The amorphous S(−)-lansoprazole (400 mg) obtained in Reference Example 3 was dissolved in ethanol (20 mL), and the resulting solution was decolorized by treatment with an activated charcoal to obtain a yellow amorphous material (320 mg). The thus-obtained amorphous material (40 mg) was dissolved in isopropanol (0.3 mL) and was mixed with n-hexane (1 mL). The mixture was kept in a refrigerator for one week, and the thus-obtained single crystals were subjected to the X-ray structure analysis to reveal that the absolute configuration of the sulfoxide is the S configuration according to a judgment method by the use of the Flack parameters.

TABLE 1

Crystal data and parameters for structure refinement

| | |
|---|---|
| Molecular formula: | $C_{16}H_{14}N_3O_2F_3S$ |
| Molecular weight: | 369.36 |
| Color and shape of the crystal: | colorless, plate |
| Size: | 0.40 × 0.20 × 0.20 (mm) |
| Crystal system: | monoclinic |
| Cell parameters: | a = 8.545 (1) (Å) |
| | b = 23.3495 (2) (Å) |
| | c = 8.723 (1) (A) |
| | β = 103.88 (1) (°) |
| | V = 1689.8 (4) (Å$^3$) |
| Space group: | P2$_1$ |
| Z: | 4 |
| Density (calculated): | 1.452 (g/cm$^3$) |
| The number of effective reflections/the number of parameters: | 11.22 |
| R (I ≧ 2σ (I)): | 0.037 |
| Flack parameters: | 0.02 (2) |

EXAMPLE 2

Crystals of (S)-2-[[[3-Methyl-4-(2,2,2-trifluoroethoxy)-2-pyridinyl]methyl]sulfinyl]-1H-benzimidazole (S(−)-Lansoprazole)

To the amorphous (S)-2-[[[3-methyl-4-(2,2,2-trifluoroethoxy)-2-pyridinyl]methyl]sulfinyl]-1H-benzimidazole (9.04 g) obtained in Reference Example 2, which was dissolved in acetone (25 mL), was added water (15 mL) with slight heating. The resulting mixture was allowed to stand at room temperature overnight, was then mixed with water (10 mL) and was sonicated. The solid material was collected by filtration, washed with water (35 mL, 25 mL) and then washed with diisopropyl ether (10 mL). The resulting material was dried under reduced pressure to obtain a solid material (8.51 g). A solution of the thus-obtained solid material (8.41 g) in acetone (30 mL) was filtered, and diisopropyl ether (50 mL) was then added to the filtrate. Small crystals were added therein and the resulting mixture was allowed to stand at room temperature overnight. The precipitated crystals were collected by filtration and were washed three times with diisopropyl ether (10 mL). The resulting crystals were dried under reduced pressure to obtain crystals (6.39 g). The thus-obtained crystals (6.39 g) were dissolved in acetone (35 mL) and water (30 mL) with heating, and the resulting solution was allowed to stand at room temperature for 1 hour. The precipitated crystals were collected by filtration, were washed with acetone-water (1:4) (15 mL) and were dried under reduced pressure to obtain crystals (3.54 g). The thus-obtained crystals (3.54 g) were dissolved in acetone (4 mL) with heating and thereto was added diisopropyl ether (14 mL). The resulting mixture was allowed to stand at room temperature for 30 minutes and was then sonicated. The precipitated crystals were collected by filtration, were washed twice with diisopropyl ether and were dried under reduced pressure to obtain the crystals of S(−)-lansoprazole (3.33 g, optical purity 99.4% ee).

mp: 146.0–147.0° C. (decomposed).

Elemental analysis

Calcd.: C, 52.03; H, 3.82; N, 11.38; S, 8.68; F, 15.43; O, 8.66.

Found: C, 51.96; H, 4.06; N, 11.20; S, 8.88; F, 15.40.

$^1$H-NMR: 2.24 (3H, s), 4.39 (2H, q, J=7.8 Hz), 4.72 (1H, d, J=13.9 Hz), 4.87 (1H, d, J=13.9 Hz), 6.68 (1H, d, J=5.8 Hz), 7.27–7.37 (2H, m), 7.48 (1H, m), 7.79 (1H, m), 8.36 (1H, d, J=5.8 Hz).

IR (ν cm$^{-1}$): 3083, 3036, 2967, 1584, 1478, 1441, 1306, 1267, 1163.

UV$_{max}$ (CHCl$_3$): 283.9 nm. [α]$_D$=−179.1° (c=0.995%, CHCl$_3$).

TABLE 2

Data of powder X-ray diffraction

| 2θ (°) | Half-valence breadth | d Value (Å) | Relative intensity (%) |
|---|---|---|---|
| 7.560 | 0.141 | 11.6841 | 92 |
| 13.040 | 0.141 | 6.7836 | 65 |
| 15.140 | 0.165 | 5.8471 | 49 |
| 15.440 | 0.141 | 5.7342 | 100 |
| 20.020 | 0.165 | 4.4315 | 32 |
| 21.700 | 0.141 | 4.0920 | 99 |
| 22.540 | 0.141 | 3.9414 | 30 |
| 22.780 | 0.165 | 3.9004 | 24 |
| 24.080 | 0.141 | 3.6927 | 46 |
| 26.120 | 0.188 | 3.4088 | 39 |
| 28.680 | 0.282 | 3.1100 | 28 |

EXAMPLE 3

Crystals of (S)-2-[[[3-Methyl-4-(2,2,2-trifluoroethoxy)-2-pyridinyl]methyl]sulfinyl]-1H-benzimidazole (S(−)-Lansoprazole) 1.5 Hydrate To the amorphous (S)-2-[[[3-methyl-4-(2,2,2-trifluoroethoxy)-2-pyridinyl]methyl]sulfinyl]-1H-benzimidazole (100 mg) obtained in Reference Example 2, which was dissolved in acetone (2 mL), was added water (2 mL). An insoluble material was removed by filtration and acetone was then allowed to be gradually evaporated from the filtrate. Small crystals were added therein and the resulting mixture was allowed to stand at room temperature overnight. The precipitated crystals were collected by filtration, were washed twice with diisopropyl ether (1 mL) and were dried under reduced pressure to obtain the crystals of (S)-2-[[[3-methyl-4-(2,2,2-trifluoroethoxy)-2-pyridinyl]methyl]sulfinyl]-1H-benzimidazole (S(−)-lansoprazole) 1.5 hydrate (62 mg).

mp: 80.0–84.0° C.;

Elemental analysis;

Calcd.: C, 48.48; H, 4.32; N, 10.60; S, 8.09; F, 14.38; O, 14.13.

Found: C, 48.48; H, 4.28; N, 10.67.

TABLE 3

Data of powder X-ray diffraction

| 2θ (°) | Half-valence breadth | d Value (Å) | Relative intensity (%) |
|---|---|---|---|
| 6.680 | 0.141 | 13.2212 | 16 |
| 9.200 | 0.141 | 9.6046 | 30 |
| 9.960 | 0.165 | 8.8734 | 59 |

TABLE 3-continued

Data of powder X-ray diffraction

| 2θ (°) | Half-valence breadth | d Value (Å) | Relative intensity (%) |
|---|---|---|---|
| 10.980 | 0.165 | 8.0513 | 49 |
| 13.380 | 0.165 | 6.6120 | 36 |
| 14.960 | 0.141 | 5.9170 | 42 |
| 15.680 | 0.165 | 5.6469 | 100 |
| 17.660 | 0.212 | 5.0180 | 73 |
| 19.720 | 0.212 | 4.4982 | 42 |
| 24.900 | 0.141 | 3.5729 | 26 |
| 29.780 | 0.235 | 2.9976 | 17 |

Industrial Applicability

The crystals of the present invention possess an excellent antiulcer action, an anti-gastric acid secreting action, a mucous membrane protecting action, an anti-*Helicobacter pylori* action and the like, and is useful as drugs owing to the low toxicity. Moreover, crystallization of the S-form not only increases the stability but also facilitates the handling of the compound, thereby making it possible to manufacture the solid pharmaceutical compositions in a reproducible manner. Also, a shorter duration of the effect is obtained in the case of the administration of the crystals of the present invention, resulting in allowing a long-term administration.

What is claimed is:

1. Crystals of (s)-2-[[[3-methyl-4-(2,2,2-trifluoroethoxy)-2-pyridinyl]methyl]sulfinyl]-1H-benzimidazole which possess a powder X-ray diffraction pattern whose characteristic peaks appear as the lattice spacing (d) of the powder X-ray diffraction at 11.68, 6.78, 5.85, 5.73, 4.43, 4.09, 3.94, 3.90, 3.69, 3.41, 3.11 angstrom.

2. A pharmaceutical composition comprising the crystals of claim 1 together with a pharmaceutically acceptable carrier.

3. Crystals of (S)-2-[[[3-methy]4-(2,2,2-trifluoroethoxy)-2-pyridinyl]methyl]sulfinyl]-1H-benzimidazole 1.5 hydrate which possess a powder X-ray diffraction pattern whose characteristic peaks appear as the lattice spacing (d) of the powder X-ray diffraction at 13.22, 9.60, 8.87, 8.05, 6.61, 5.92, 5.65, 5.02, 4.50, 3.57, 3.00 angstrom.

4. A pharmaceutical composition comprising the crystals of claim 3 together with a pharmaceutically acceptable carrier.

* * * * *